Sept. 6, 1966 W. E. DUFFETT Plant Pat. 2,670
CHRYSANTHEMUM PLANT
Filed Aug. 19, 1965
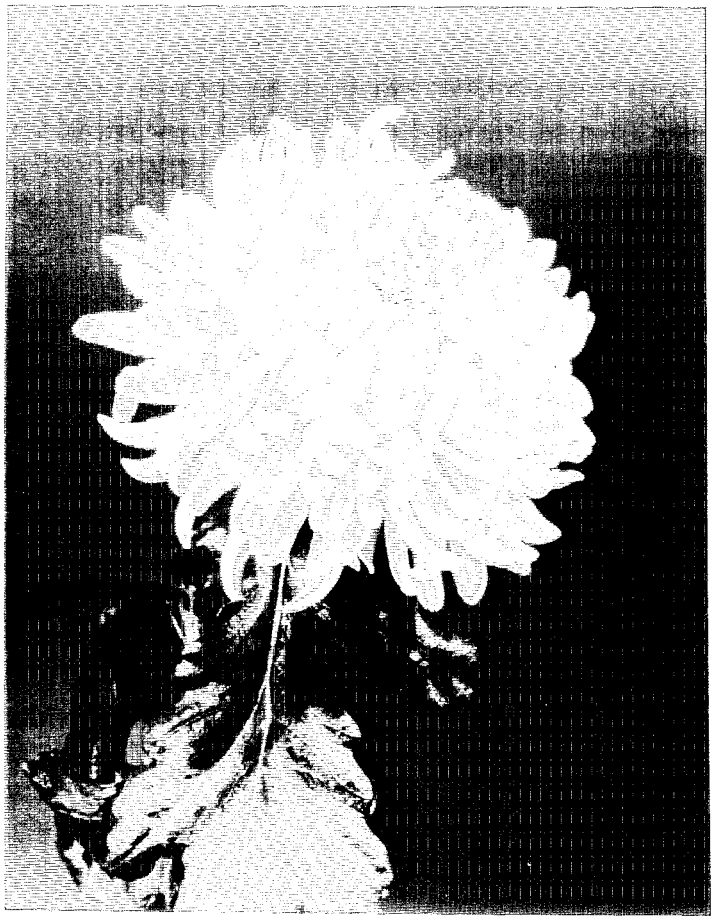
INVENTOR:
W. E. DUFFETT
by Robb & Robb
attorneys

United States Patent Office

Plant Pat. 2,670
Patented Sept. 6, 1966

2,670
CHRYSANTHEMUM PLANT

William E. Duffett, Barberton, Ohio, assignor to Orville O. Dunham, Niles, Mich.

Filed Aug. 19, 1965, Ser. No. 481,153
1 Claim. (Cl. Plt.—78)

My present invention comprises a new and distinct variety of chrysanthemum plant which is a sport of the plant disclosed in Plant Patent No. 2,002.

The parent variety of the plant hereof, was the result of a long period of hybridization, in which many crosses and careful selection produced such parent variety, and the instant variety was discovered during the growth of the parent variety on a production basis.

While the conditions which produced the instant variety are somewhat different in view of the fact that the parent was hybridized at Niles, Michigan, the variety hereof, was grown in production after it was discovered as a sport at Barberton, Ohio.

The outstanding difference of the instant variety from the parent, is the color of the blooms and a further distinctive characteristic is the substantially shorter growth habit, the other characteristics of the plant being very much the same.

The color of my new variety determined by appropriate reference to color charts and specifically the blooms of my new variety are of a strong orange-yellow color (Nickerson Color Fan published by Munsell Color Company). As grown in the vicinity of Barberton, Ohio, under uniform culture, plants of my new variety produce very large flowers with somewhat shorter growth habit as before noted than related varieties although similar in most aspects to the parent as before noted likewise.

Under conditions of culture previously mentioned which were undertaken in the vicinity of Barberton, Ohio, my new variety blooms from mid-September, profusely and almost continuously, with light frost tending to accentuate the color and the blooms lasting until a killing frost.

Blooms of my new variety have in many cases and in fact are largely productive of sizes which approximate 7 inches in diameter, are born in clusters, the clusters being somewhat pyramidal.

My new variety has been asexually reproduced by stem cuttings, in the vicinity of Barberton, Ohio, and Niles, Michigan.

My new variety has been found to retain its distinctive characteristics through successive asexual reproduction.

The accompanying drawing, forming a part hereof, shows a typical plant of my new variety of chrysanthemum.

Following is a detailed description of my new variety of chrysanthemum plant, the color references being to the Nickerson Color Fan produced by Munsell Color Company:

Parentage: Sport of Plant Patent No. 2,002.

Classification: Botanic—*Chrysanthemum indicum.*

*Flower*

Blooming habit: Blooms profusely from mid-September until a killing frost and almost continuously during that period. Observations were made in the vicinity of Barberton, Ohio in mid-October.

Bud:

*Size.*—Large.
*Form.*—Short with flat top; not very much affected by hot or wet weather.
*Sepals.*—Of little or no consequence.
*Peduncle.*—Length is very long.
*Aspect.*—Rough.
*Strength.*—Stiff and direct.
While the bud opens well it is somewhat affected by adverse conditions.

Bloom:

*Size.*—Very large. Average size when fully expanded—7" disbudded.
*Borne.*—In clusters and somewhat irregularly.
*Stems.*—Long and strong.
*Form.*—Retains its form to the end of bloom period.
*Petalage.*—Very double with too many petals to count under normal conditions.
*Color.*—Center of flower—10YR 8/10 moderate orange yellow. Outer petals—10YR 7/10 strong orange yellow. Base of petals—10YR 7/10 strong orange yellow. Inside of petals—10R 4/9 dark reddish-orange. Reverse of petals—7.5Y 9/8 brilliant greenish-yellow. General tonality from a distance—10YR 7/10 strong orange yellow.
*Discoloration.*—General tonality at end of: First week—retains much the same color. Second week—retains somewhat the same color. Third week—retains somewhat the same color and light frost tends to intensify color.

Petals:

*Texture.*—Thin. Wet weather tends to bleach and hot weather occasionally develops a fungus infection.
*Appearance.*—Inside—velvety. Outside—satiny.
*Form.*—Pointed.
*Arrangement.*—Imbricated.
*Persistence.*—Hang on and dry.
*Fragrance.*—None.
*Lastingness.*—On the plant—very long. As cut flowers—long.

Genital organs:

*Stamens, anthers.*—Small and few.
*Arrangement.*—Regular around styles.
*Stamens, filaments.*—Short.
*Styles.*—Columnar and short.
*Ovaries.*—All enclosed in calyx.

*Plant*

Form: Bush.
Growth: Vigorous upright branching and compact.
Height: 24 inches.

Foliage:

*Leaflets.*—Alternate.
*Size.*—Large.
*Quantity.*—Abundant.
*Shape.*—3 lobed.
*Texture.*—Smooth upper side—smooth and flat.
*Ribs and veins.*—Ordinary.
*Edge.*—Smooth.

I claim:

A new and distinct variety of chrysanthemum plant substantially as herein disclosed, characterized as to novelty by the strong orange yellow color of its blooms, the very double arrangement of its petals, and the shorter growth habit than its parent.

No references cited.

ABRAHAM G. STONE, *Primary Examiner.*

R. E. BAGWILL, *Assistant Examiner.*